US012810634B2

(12) United States Patent
Hattori et al.

(10) Patent No.: US 12,810,634 B2
(45) Date of Patent: Nov. 24, 2026

(54) IMAGE DIAGNOSIS METHOD, IMAGE DIAGNOSIS SUPPORT DEVICE, AND COMPUTER SYSTEM

(71) Applicants: HITACHI HIGH-TECH CORPORATION, Tokyo (JP); JAPANESE FOUNDATION FOR CANCER RESEARCH, Tokyo (JP)

(72) Inventors: Hideharu Hattori, Tokyo (JP); Yasuki Kakishita, Tokyo (JP); Kenko Uchida, Tokyo (JP); Toshinari Sakurai, Tokyo (JP); Futoshi Akiyama, Tokyo (JP)

(73) Assignees: Hitachi High-Tech Corporation, Tokyo (JP); Japanese Foundation For Cancer Research, Tokyo (JP)

( * ) Notice: Subject to any disclaimer, the term of this patent is extended or adjusted under 35 U.S.C. 154(b) by 1004 days.

(21) Appl. No.: 17/928,735

(22) PCT Filed: Mar. 8, 2021

(86) PCT No.: PCT/JP2021/009063
§ 371 (c)(1),
(2) Date: Nov. 30, 2022

(87) PCT Pub. No.: WO2021/246013
PCT Pub. Date: Dec. 9, 2021

(65) Prior Publication Data

US 2023/0237818 A1 Jul. 27, 2023

(30) Foreign Application Priority Data

Jun. 3, 2020 (JP) ................................ 2020-097112

(51) Int. Cl.
*G06K 9/00* (2022.01)
*A61B 5/00* (2006.01)
(Continued)

(52) U.S. Cl.
CPC .......... *G06V 20/698* (2022.01); *A61B 5/7264* (2013.01); *G01N 33/4833* (2013.01);
(Continued)

(58) Field of Classification Search
CPC ...... G06V 10/22; G06V 10/25; G06V 10/255; G06V 10/26; G06V 10/40; G06V 10/42;
(Continued)

(56) References Cited

U.S. PATENT DOCUMENTS

2009/0060297 A1 3/2009 Penn et al.
2011/0274340 A1 11/2011 Suzuki et al.
(Continued)

FOREIGN PATENT DOCUMENTS

CN 107430757 A 12/2017
JP 2010-203949 A 9/2010
(Continued)

OTHER PUBLICATIONS

International Search Report, PCT/JP2021/009063, dated May 18, 2021. 3 pages.
(Continued)

*Primary Examiner* — Eric Rush
(74) *Attorney, Agent, or Firm* — Volpe Koenig

(57) ABSTRACT

An image diagnosis method comprises a step of acquiring an image including at least one of a tissue and a cell as an element, a step of classifying, for each partial image that is a part of the image, a property of the element included in the partial image, and a step of sorting the image into any one of benign indicating that no lesion element is present, malignant indicating that a lesion element is present, and follow-up based on classification results of the plurality of partial images.

14 Claims, 7 Drawing Sheets

(51) Int. Cl.

| | |
|---|---|
| ***G01N 33/483*** | (2006.01) |
| ***G06T 7/00*** | (2017.01) |
| ***G06T 7/62*** | (2017.01) |
| ***G06V 10/22*** | (2022.01) |
| ***G06V 10/44*** | (2022.01) |
| ***G06V 10/50*** | (2022.01) |
| ***G06V 10/70*** | (2022.01) |
| ***G06V 10/764*** | (2022.01) |
| ***G06V 10/77*** | (2022.01) |
| ***G06V 10/80*** | (2022.01) |
| ***G06V 20/69*** | (2022.01) |
| ***G16H 30/40*** | (2018.01) |
| ***G16H 50/20*** | (2018.01) |

(52) U.S. Cl.
CPC .............. *G06T 7/0012* (2013.01); *G06T 7/62* (2017.01); *G06V 10/22* (2022.01); *G06V 10/454* (2022.01); *G06V 10/50* (2022.01); *G06V 10/70* (2022.01); *G06V 10/764* (2022.01); *G06V 10/7715* (2022.01); *G06V 10/806* (2022.01); *G06V 10/809* (2022.01); *G06V 20/69* (2022.01); *G16H 30/40* (2018.01); *G16H 50/20* (2018.01); *G06T 2207/20021* (2013.01); *G06T 2207/30024* (2013.01); *G06T 2207/30096* (2013.01)

(58) Field of Classification Search
CPC .... G06V 10/44; G06V 10/443; G06V 10/454; G06V 10/50; G06V 10/70; G06V 10/74; G06V 10/75; G06V 10/764; G06V 10/7715; G06V 10/80; G06V 10/803; G06V 10/806; G06V 10/809; G06V 10/811; G06V 10/817; G06V 10/82; G06V 20/69; G06V 20/695; G06V 20/698; G06V 20/70; G06V 2201/03; G06V 2201/032; G06T 7/0012; G06T 7/10; G06T 7/11; G06T 7/136; G06T 7/143; G06T 7/50; G06T 7/60; G06T 7/62; G06T 7/70; G06T 2207/10056; G06T 2207/20021; G06T 2207/20076; G06T 2207/20081; G06T 2207/20084; G06T 2207/20112; G06T 2207/30004; G06T 2207/30024; G06T 2207/30068; G06T 2207/30096; G16H 30/40; G16H 50/20; G01N 33/48; G01N 33/483; G01N 33/4833; A61B 5/055; A61B 5/1079; A61B 5/72; A61B 5/7246; A61B 5/725; A61B 5/7264; A61B 5/7267; A61B 5/742; A61B 5/743; A61B 6/50; A61B 6/501; A61B 6/502; A61B 6/5217; A61B 8/0825; A61B 8/085; A61B 8/485; A61B 8/52; A61B 8/5215; A61B 8/5223
USPC ....... 382/100, 103, 128, 133, 134, 159, 164, 382/165, 170, 171, 173, 181, 190, 192, 382/195, 203, 224–228, 282, 286, 291
See application file for complete search history.

(56) References Cited

U.S. PATENT DOCUMENTS

| | | | | |
|---|---|---|---|---|
| 2012/0004514 | A1 | 1/2012 | Marugame | |
| 2013/0071003 | A1 | 3/2013 | Wirtz et al. | |
| 2016/0117818 | A1* | 4/2016 | Park | G06T 7/0012 382/131 |
| 2016/0232425 | A1* | 8/2016 | Huang | G06T 7/0012 |
| 2018/0053296 | A1 | 2/2018 | Hattori et al. | |
| 2019/0080454 | A1* | 3/2019 | Hameed | G06T 7/0014 |
| 2019/0279760 | A1* | 9/2019 | Yao | G06T 7/0012 |
| 2020/0250814 | A1* | 8/2020 | Stoval, III | G06T 7/0012 |
| 2021/0104042 | A1 | 4/2021 | Fukuda et al. | |
| 2021/0350534 | A1* | 11/2021 | Endo | G06T 7/0012 |
| 2021/0407655 | A1* | 12/2021 | Ohyu | G06T 7/0012 |
| 2022/0076410 | A1* | 3/2022 | Georgescu | G06T 7/0012 |

FOREIGN PATENT DOCUMENTS

| | | | | |
|---|---|---|---|---|
| JP | 2021-58270 | A | 4/2021 | |
| WO | 2010/087112 | A1 | 8/2010 | |
| WO | 2017/150497 | A1 | 9/2017 | |
| WO | WO-2018084071 | A1 * | 5/2018 | G06T 7/0012 |
| WO | WO-2018186052 | A1 * | 10/2018 | G06T 7/0012 |

OTHER PUBLICATIONS

Chinese Office Action issued on Nov. 1, 2025 for Chinese Patent Application No. 202180039706.7.

* cited by examiner

[FIG. 1]
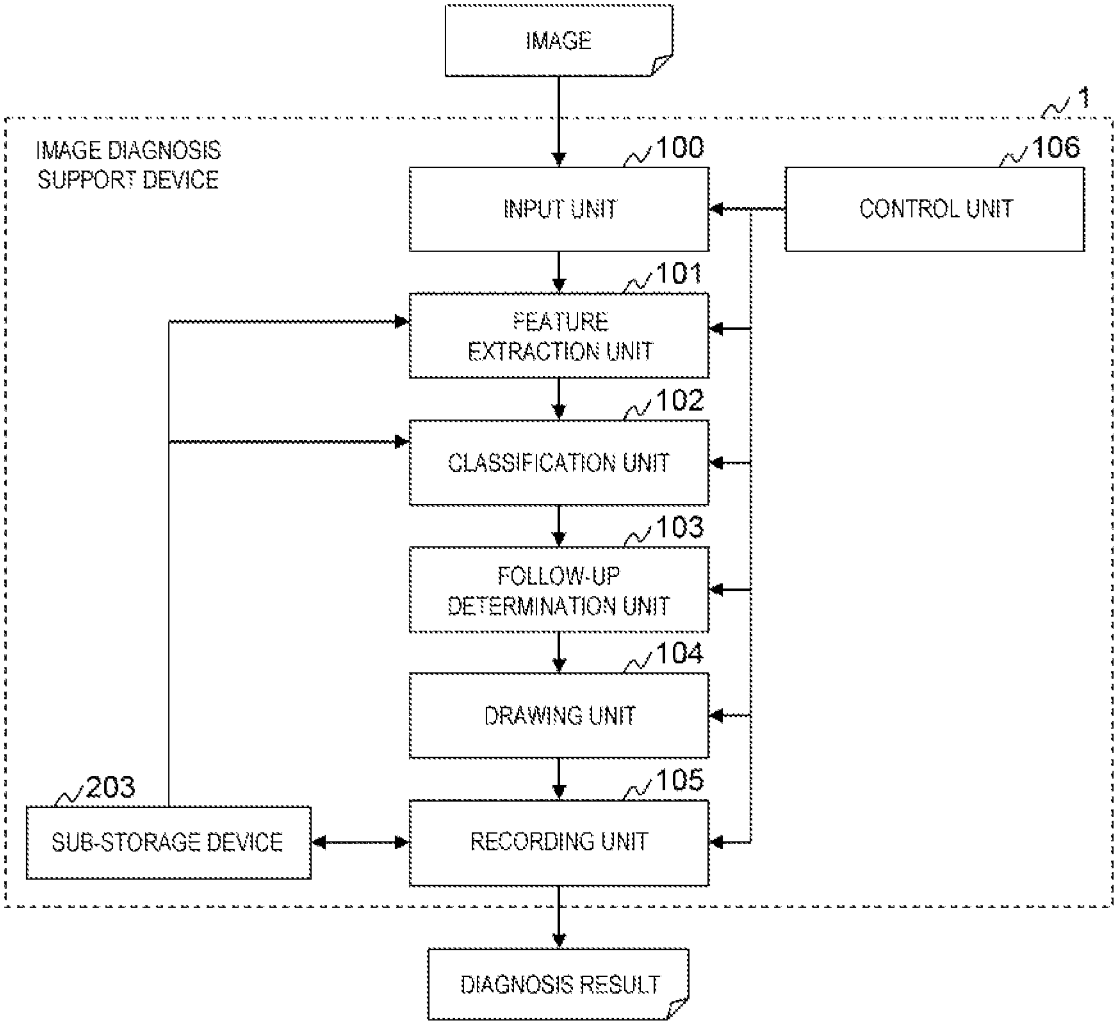

[FIG. 2]
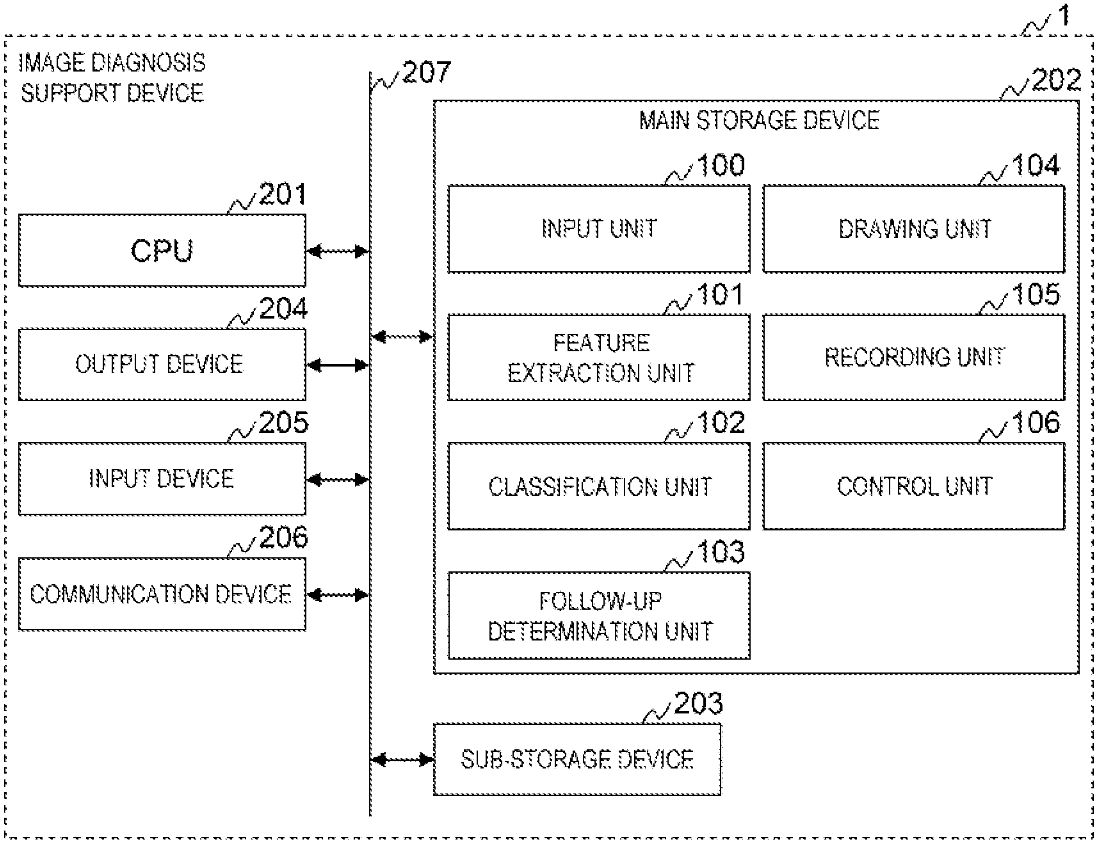

[FIG. 3]
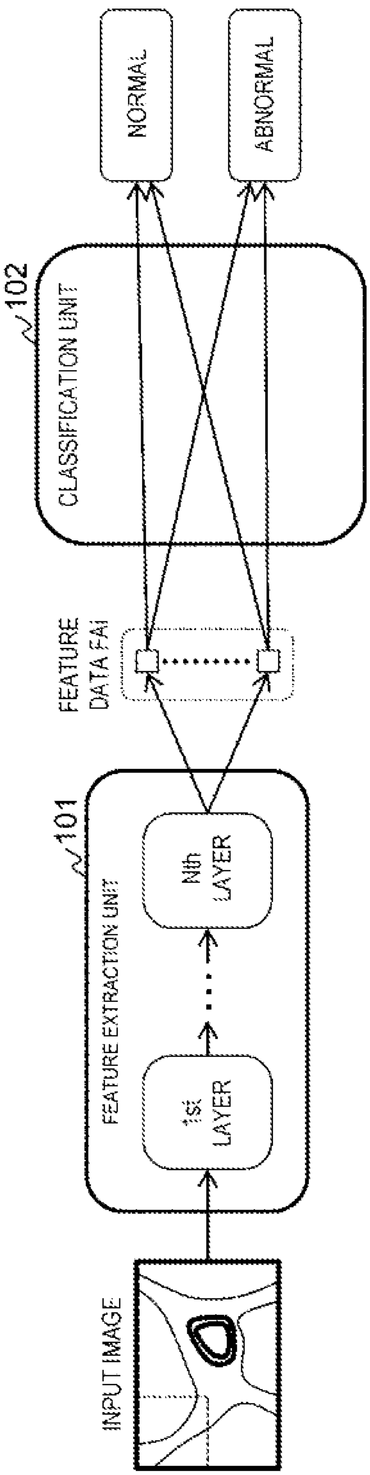

[FIG. 4]
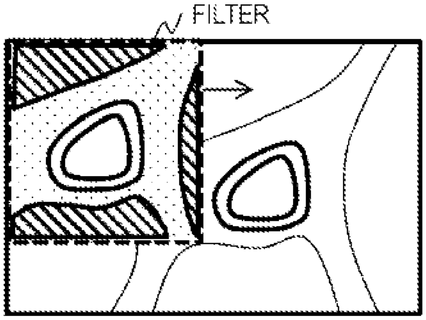
[FIG. 5A]
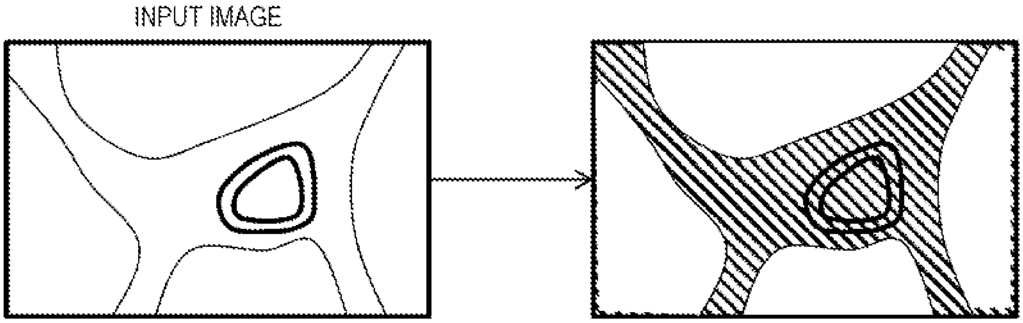
[FIG. 5B]
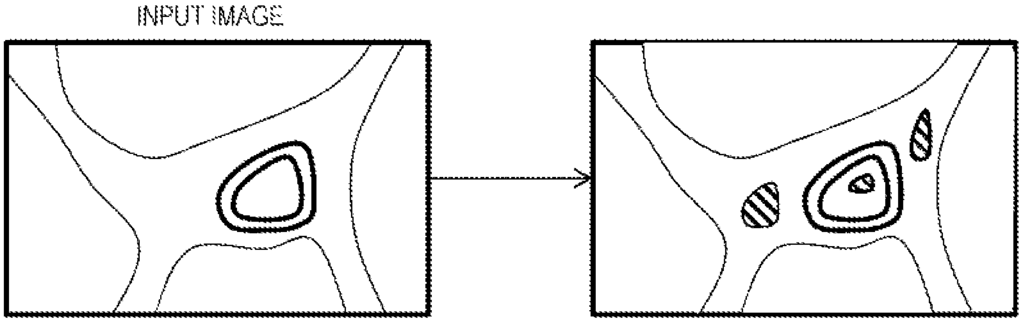

[FIG. 6A]
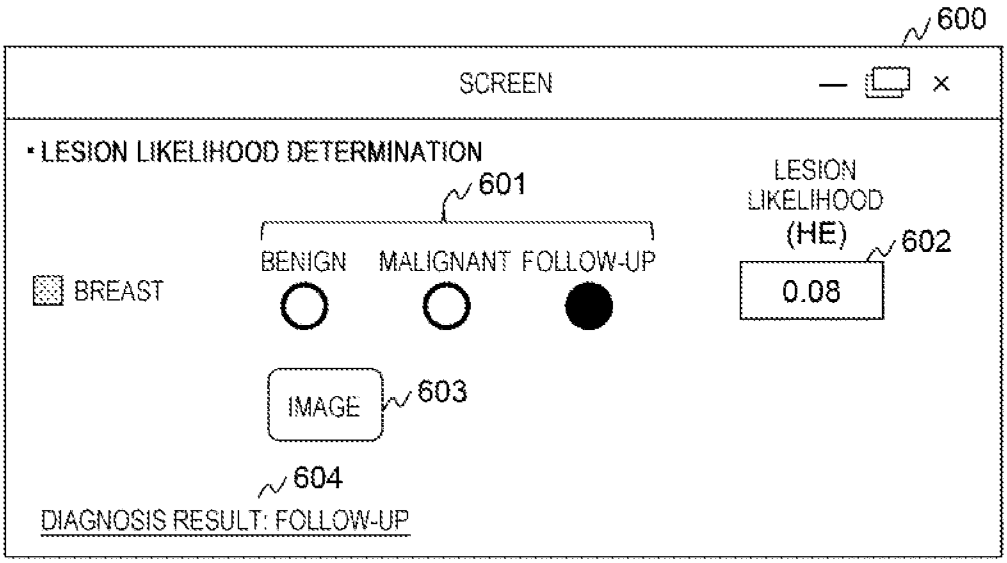
[FIG. 6B]
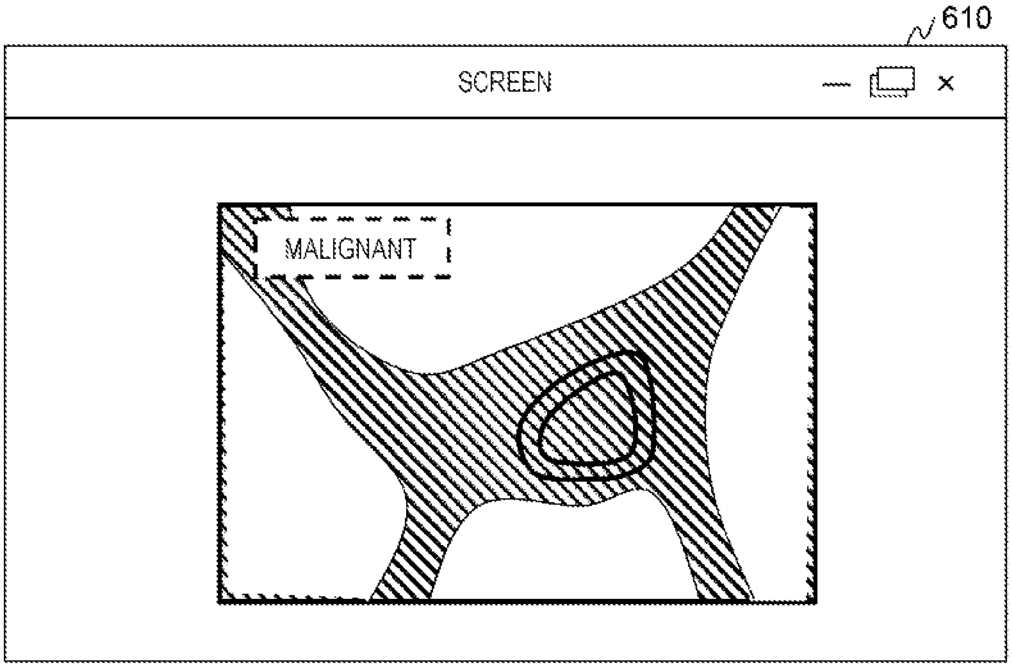

[FIG. 7]
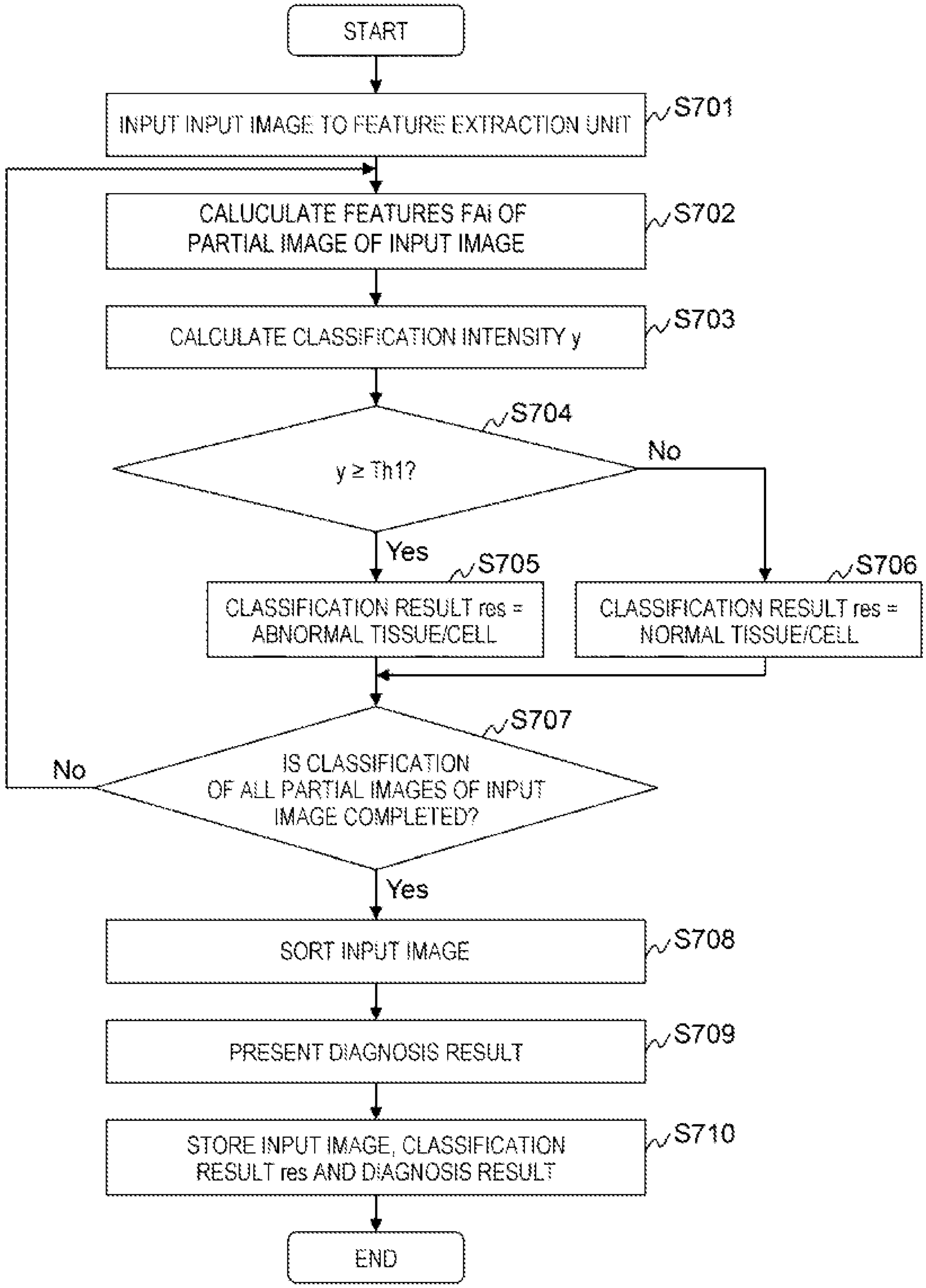

[FIG. 8]
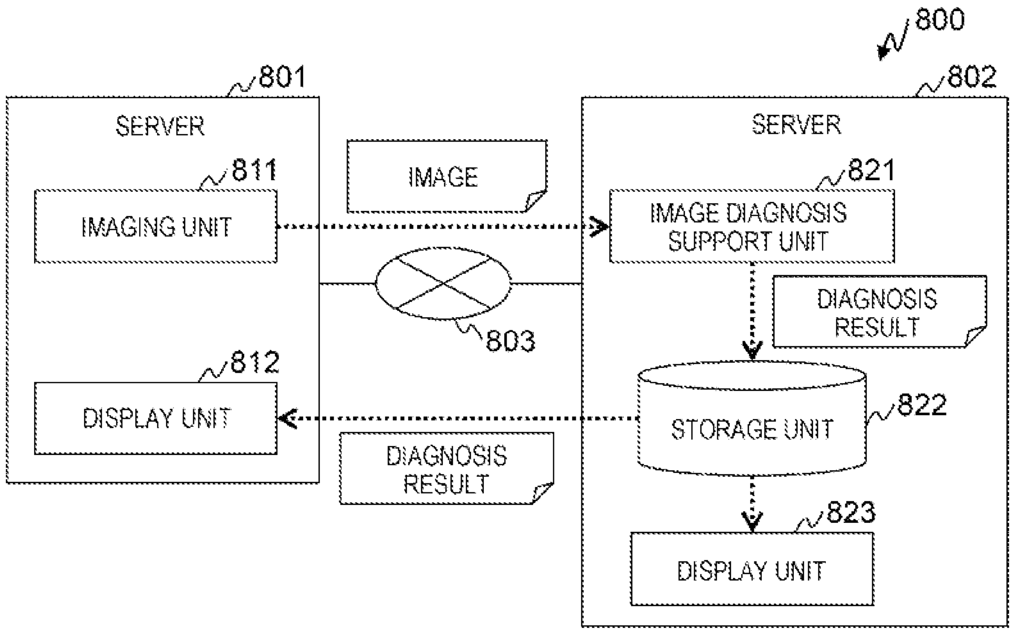
[FIG. 9]
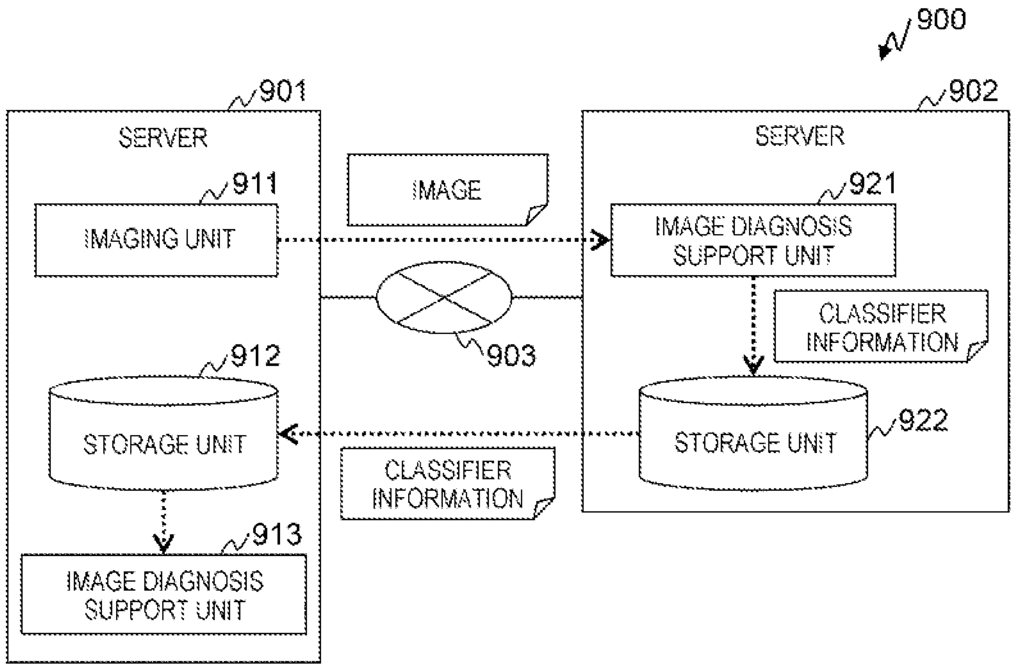

IMAGE DIAGNOSIS METHOD, IMAGE DIAGNOSIS SUPPORT DEVICE, AND COMPUTER SYSTEM

CROSS-REFERENCE TO RELATED APPLICATIONS

The present application claims priority of Japanese Patent Application No. 2020-97112 filed on Jun. 3, 2020, the contents of which are incorporated herein by reference.

TECHNICAL FIELD

The present invention relates to an image diagnosis method, device, and system for detecting a specific tissue or cell using an image.

BACKGROUND ART

In recent years, "pathological diagnosis" by microscopic observation of a lesion tissue specimen plays an important role in disease diagnosis. In pathological diagnosis, most of work from specimen preparation to diagnosis is manually performed, and is difficult to be automated. In particular, ability and experience are important factors for accurate diagnosis, and accuracy of diagnosis depends on ability of a pathologist. On the other hand, pathologists are insufficient in the medical field due to factors such as an increase of cancer patients along with aging of the population. Therefore, there is an increasing need for an image processing technique of supporting pathological diagnosis, remote diagnosis, and the like.

For example, a technique disclosed in PTL 1 is known as the technique of supporting pathological diagnosis as described above. PTL 1 discloses that "an image diagnosis support device includes an image data acquisition unit that acquires high-magnification image data of a specimen tissue, and the image diagnosis support device includes: an image sorting unit that generates low-magnification image data from the high-magnification image data acquired by the image data acquisition unit, and sorts the generated low-magnification image data into a group of each image data pattern of a plurality of pathological tissues; and an image determination unit that determines whether the high-magnification image data serving as a source of the low-magnification image data sorted by the image sorting unit is a pathological tissue in the sorted group."

CITATION LIST

Patent Literature

PTL 1: JP-A-2010-203949

SUMMARY OF INVENTION

Technical Problem

In the related art, whether a tissue/cell is an abnormal tissue/cell (for example, tissue/cell indicating malignant) or a benign tissue/cell is determined based on an image including the tissue/cell. However, actually, it is difficult to determine whether it is abnormal or benign, and it is better to carry out follow-up in some cases. In such a case, when abnormal or benign is determined, detection omission of an abnormal tissue/cell (overlooking of malignant tissue/cell) or erroneous detection of an abnormal tissue/cell may occur. The detection omission of the abnormal tissue/cell may lead to aggravation of a symptom, and the erroneous detection of the abnormal tissue/cell may result in erroneous site excision.

The invention has been made in view of such circumstances, and an object thereof is to provide a technique of presenting not only malignant and benign but also follow-up as a diagnosis result based on an image including a tissue/cell.

Solution to Problem

A representative example of the invention disclosed in the present application is outlined as follows. That is, there is provided an image diagnosis method executed by an image diagnosis support device. The image diagnosis support device includes an arithmetic device, a storage device, and a connection interface configured to connect to an external device. The image diagnosis method includes: a step of, by the arithmetic device, acquiring an image including at least one of a tissue and a cell as an element via the connection interface, and storing the image in the storage device; a step of, by the arithmetic device, classifying, for each partial image that is a part of the image, a property of the element included in the partial image, and storing a classification result in the storage device; a step of, by the arithmetic device, sorting the image into any one of benign indicating that no lesion element is present, malignant indicating that a lesion element is present, and follow-up based on classification results of the plurality of partial images, and storing a sorting result as a diagnosis result in the storage device; and a step of outputting, by the arithmetic device, the diagnosis result via the connection interface.

Advantageous Effects of Invention

According to the invention, the image diagnosis support device can present, as a diagnosis result, any one of malignant, benign, and follow-up based on an image. Problems, configurations, and effects other than those described above will be apparent from the following description of embodiments.

BRIEF DESCRIPTION OF DRAWINGS

FIG. 1 is a block diagram showing an example of a functional configuration of an image diagnosis support device 1 according to a first embodiment.

FIG. 2 is a diagram showing an example of a hardware configuration of the image diagnosis support device 1 according to the first embodiment.

FIG. 3 is a diagram showing specific configurations of a feature extraction unit and a classification unit according to the first embodiment.

FIG. 4 is a diagram showing an operation of the feature extraction unit according to the first embodiment.

FIG. 5A is a diagram showing an operation of the classification unit according to the first embodiment.

FIG. 5B is a diagram showing an operation of the classification unit according to the first embodiment.

FIG. 6A is a diagram showing an example of a screen presented by a drawing unit according to the first embodiment.

FIG. 6B is a diagram showing an example of the screen presented by the drawing unit according to the first embodiment.

FIG. 7 is a flowchart showing processing executed by the image diagnosis support device according to the first embodiment.

FIG. 8 is a diagram showing an example of a configuration of a remote diagnosis support system according to a second embodiment.

FIG. 9 is a diagram showing an example of a configuration of a network consignment service providing system according to a third embodiment.

DESCRIPTION OF EMBODIMENTS

Each embodiment of the invention provides an image diagnosis support device that prevents detection omission and erroneous detection of an abnormal tissue/cell indicating a lesion tissue/cell such as a cancer by outputting any one of malignant, benign, and follow-up as a diagnosis result, and a method therefor.

Hereinafter, embodiments of the invention will be described with reference to the accompanying drawings. In the accompanying drawings, functionally identical elements may be denoted by the same reference numerals. The accompanying drawings show specific examples of implementation according to the principle of the invention, but these are for the purpose of understanding the invention and are not used to limit the invention.

While the present embodiment has been described in sufficient detail for a person skilled in the art to carry out the invention, it is necessary to understand that other implementations and forms are possible, and changes in configuration and structure and replacement of various elements are possible without departing from the scope and spirit of the technical idea of the invention. Therefore, the following description should not be construed as being limited thereto.

As will be described later, the embodiments of the invention may be implemented by software running on a general-purpose computer, or may be implemented by dedicated hardware or a combination of software and hardware.

Hereinafter, each processing in the embodiments of the invention will be described with "each processing unit (for example, feature extraction unit) as a program" as a subject (operation subject), but since the program executes processing determined by being executed by an arithmetic device such as a processor and a CPU while using a memory and a communication port (communication control device), the description may be made with the arithmetic device as the subject.

First Embodiment

FIG. 1 is a block diagram showing an example of a functional configuration of an image diagnosis support device 1 according to a first embodiment.

The image diagnosis support device 1 includes an input unit 100, a feature extraction unit 101, a classification unit 102, a follow-up determination unit 103, a drawing unit 104, a recording unit 105, and a control unit 106.

The input unit 100, the feature extraction unit 101, the classification unit 102, the follow-up determination unit 103, the drawing unit 104, the recording unit 105, and the control unit 106 may be implemented by programs or by modularization.

The input unit 100 receives an input of an image. For example, the input unit 100 may receive, as input images, still images or the like encoded in JPG, Jpeg 2000, PNG, BMP formats, or the like captured at predetermined intervals by an imaging unit such as a camera built in a microscope. The input unit 100 may extract still images of frames at predetermined intervals from a moving image in Motion JPEG, MPEG, H.264, HD/SDI formats, or the like, and receive the still images as input images. The input unit 100 may receive, as an input image, an image acquired by an imaging unit via a bus, a network, or the like. The input unit 100 may receive, as an input image, an image stored in a detachable recording medium.

The feature extraction unit 101 acquires definition information on an algorithm (model) stored in a sub-storage device 203, and extracts, using the algorithm, features related to a tissue/cell from a partial image that is a part of an image (input image) including the tissue/cell.

The classification unit 102 acquires definition information on an algorithm (model) stored in the sub-storage device 203, and calculates, using the algorithm and the features, a classification intensity representing likelihood of a normal tissue/cell (for example, benign tissue/cell) and a classification intensity representing likelihood of an abnormal tissue/cell (for example, malignant tissue/cell) for each partial image of the input image. That is, a value indicating a degree corresponding to a certain property of the tissue/cell is calculated. The classification unit 102 outputs a classification result of benign or malignant of each partial image based on the classification intensity.

The follow-up determination unit 103 calculates an area (classification area) of each classification result in the input image based on the classification result of each partial image. The follow-up determination unit 103 sorts the input image into any one of malignant, benign, and follow-up based on the classification intensity and the classification area of each partial image.

The drawing unit 104 displays an image representing a distribution of the classification intensities of the classification results calculated by the classification unit 102. The drawing unit 104 displays, for example, an input image that is color-coded corresponding to each classification result. The drawing unit 104 displays a sorting result (diagnosis result) obtained by the follow-up determination unit 103.

The recording unit 105 stores the image and the diagnosis result displayed by the drawing unit 104 in the sub-storage device 203 (see FIG. 2).

The control unit 106 controls the entire image diagnosis support device 1. The control unit 106 is connected to the input unit 100, the feature extraction unit 101, the classification unit 102, the follow-up determination unit 103, the drawing unit 104, and the recording unit 105. Each functional unit of the image diagnosis support device 1 operates autonomously or according to an instruction from the control unit 106.

The image diagnosis support device 1 according to the first embodiment extracts, using the feature extraction unit 101, features indicating abnormality likelihood of a tissue/cell included in an input image, and calculates, using the classification unit 102, a classification intensity indicating a degree of normality likelihood and the abnormality likelihood of the tissue/cell for the input image. Further, the image diagnosis support device 1 calculates a classification area for each classification result (normal and abnormal) using the follow-up determination unit 103, and sorts any one of malignant, benign, and follow-up into a class using the classification intensity and the classification area of a classification result of each partial image.

For the functional units in the image diagnosis support device 1, a plurality of functional units may be integrated into one functional unit, or one functional unit may be divided into a plurality of functional units for each function.

For example, the feature extraction unit 101 may be provided in the classification unit 102.

The image diagnosis support device 1 may be implemented not as a device but as a function. In this case, the function may be implemented in a tissue/cell image acquisition device such as a virtual slide, or may be implemented in a server connected to a tissue/cell image acquisition device via a network as described in second and third embodiments.

FIG. 2 is a diagram showing an example of a hardware configuration of the image diagnosis support device 1 according to the first embodiment.

The image diagnosis support device 1 includes a CPU 201, a main storage device 202, the sub-storage device 203, an output device 204, an input device 205, and a communication device 206. The pieces of hardware described above are interconnected via a bus 207.

The CPU 201 is an example of an arithmetic device, reads a program from the main storage device 202 as necessary, and executes the program.

The main storage device 202 is a storage device such as a memory, and stores programs for implementing the input unit 100, the feature extraction unit 101, the classification unit 102, the follow-up determination unit 103, the drawing unit 104, the recording unit 105, and the control unit 106. The main storage device 202 includes a work area to be temporarily used by the program.

The sub-storage device 203 is a storage device such as a hard disk drive (HDD) or a solid state drive (SSD), and permanently stores data. The sub-storage device 203 according to the first embodiment stores the input image, the classification result and the classification intensity of each partial image of the input image output by the classification unit 102, the classification area and the diagnosis result of each classification result output by the follow-up determination unit 103, and the image generated by the drawing unit 104 (a numerical value of the classification intensity for drawing the classification intensity, and position information). The sub-storage device 203 stores information on algorithms to be used by the feature extraction unit 101 and the classification unit 102, and the like.

The output device 204 includes devices such as a display, a printer, and a speaker. For example, the output device 204 displays display data generated by the drawing unit 104 on the display.

The input device 205 includes devices such as a keyboard, a mouse, and a microphone. A user inputs various instructions such as determination of an input image and setting of parameters to the image diagnosis support device 1 using the input device 205.

The communication device 206 communicates with other devices via a network. For example, the communication device 206 receives data such as an image transmitted from a device connected via a network, such as a server, and stores the data in the sub-storage device 203. The communication device 206 is not an essential component of the image diagnosis support device 1. For example, when a communication device is provided in a computer or the like connected to an image acquisition device, the image diagnosis support device 1 may not include the communication device 206.

Next, the functional units in the image diagnosis support device 1 will be described in detail.

FIG. 3 is a diagram showing specific configurations of the feature extraction unit 101 and the classification unit 102 according to the first embodiment. FIG. 4 is a diagram showing an operation of the feature extraction unit 101 according to the first embodiment. FIGS. 5A and 5B are diagrams showing operations of the classification unit 102 according to the first embodiment. FIGS. 6A and 6B are diagrams showing examples of a screen presented by the drawing unit 104 according to the first embodiment.

First, the feature extraction unit 101 will be described.

The feature extraction unit 101 extracts features of an input image. As shown in FIG. 3, the feature extraction unit 101 calculates features of a tissue/cell included in an input image using a classifier such as an N-layer convolutional neural network (CNN). The classifier calculates the features to classify an object in the image.

For example, as shown in FIG. 4, the feature extraction unit 101 calculates features fi of a filter i by moving the filter i from an upper left side to a lower right side in an input image using a CNN that performs arithmetic processing as in Equation (1). The feature extraction unit 101 calculates a matrix of the features fi as features FAi of the tissue/cell included in the input image.

[Math. 1]

$$fi = h\left(\sum_{j=1}^{m}(pj \times wj) + bi\right) \quad (1)$$

In Equation (1), wj represents a filter coefficient, pj represents a pixel value, bi represents an offset value, m represents the number of filter coefficients, and h represents a nonlinear function. The filter coefficient wj is a coefficient of the classifier, and is calculated using a known machine learning technique such that a normal tissue/cell and an abnormal tissue/cell can be classified. The sub-storage device 203 stores parameters such as the filter coefficient wj and the offset value bi.

Next, the classification unit 102 will be described.

The classification unit 102 executes logistic regression processing using a matrix f including the features FAi calculated by the feature extraction unit 101 to calculate a value (classification intensity) indicating lesion likelihood.

The classification unit 102 calculates a classification intensity y of each classification result based on, for example, Equation (2). That is, as shown in FIG. 3, the classification unit 102 classifies whether the tissue/cell included in a partial image is normal or abnormal based on the classification intensity of each classification result, and outputs the classification result. Here, a classification result having a high classification intensity is adopted.

[Math. 2]

$$y = g(w \times f + b) \quad (2)$$

In Equation (2), w represents a weight matrix, b represents an offset value, g represents a nonlinear function, and y represents a classification intensity of a classification result. The weight matrix w and the offset value b are calculated using a known machine learning technique. For example, CNN may be used as a machine learning technique. The sub-storage device 203 stores parameters such as the weight matrix w and the offset value b.

Next, the follow-up determination unit 103 will be described.

The follow-up determination unit 103 calculates a classification area of each classification result in an input image as shown in FIGS. 5A and 5B based on a classification result of each partial image output by the classification unit 102. In FIGS. 5A and 5B, a portion of a classification result "normal" is indicated in white, and a portion of a classification result "abnormal" is indicated by oblique lines.

For example, the follow-up determination unit 103 calculates the classification area based on the total number of colors (for example, the number of pixels) in the input image. Alternatively, the follow-up determination unit 103 detects a tissue region from the input image, and calculates a classification area based on the total number of colors (for example, the number of pixels) in the tissue region.

The follow-up determination unit 103 calculates a value of lesion likelihood (HE) for the input image using the classification intensity y of the classification result of each of a plurality of partial images. The value of the lesion likelihood is a real number between 0 and 1.

The follow-up determination unit 103 determines whether the input image corresponds to any class of malignant, benign, and follow-up based on a determination condition related to the classification region of each classification result.

For example, the following determination processing may be considered.

(Step 0) The follow-up determination unit 103 determines whether there is a region where a classification intensity of a classification result "abnormal" is A1 or larger. When the above-described determination condition is satisfied, the follow-up determination unit 103 determines that a class of the input image is "malignant". When the above-described determination condition is not satisfied, the follow-up determination unit 103 proceeds to Step 1.

(Step 1) The follow-up determination unit 103 determines whether a classification area with the classification intensity of the classification result "abnormal" that is less than A1 and equal to or greater than A2 is less than B1%. When the above-described determination condition is satisfied, the follow-up determination unit 103 determines that a class of the input image is "benign". When the above-described determination condition is not satisfied, the follow-up determination unit 103 proceeds to Step 2.

(Step 2) The follow-up determination unit 103 determines whether a classification area with the classification intensity of the classification result "abnormal." that is less than A1 and equal to or greater than A2 is equal to or greater than B1% and less than B2. When the above-described determination condition is satisfied, the follow-up determination unit 103 determines that a class of the input image is "follow-up". When the above-described determination condition is not satisfied, the follow-up determination unit 103 proceeds to Step 3.

(Step 3) When a classification area with the classification intensity of the classification result "abnormal" that is less than A1 and equal to or greater than A2 is equal to or greater than B2%, the follow-up determination unit 103 determines that a class of the input image is "malignant".

A1, A2, B1, and B2 are preset thresholds. A1 and A2 are values such as 0.8 and 0.5, and B1 and B2 are values such as 5 or 10. In an example shown in FIG. 5A, when the above-described determination processing is executed, a class of the input image is determined to be "malignant". In an example shown in FIG. 5B, when the above-described determination processing is executed, a class of the input image is determined to be "follow-up".

In this way, the image diagnosis support device 1 according to the first embodiment executes determination in consideration of the classification intensity of the classification result and the area of the classification result, thereby enabling sorting of "benign" and "malignant" as well as "follow-up".

Next, the drawing unit 104 will be described.

The drawing unit 104 presents a diagnosis result together with a basis. For example, the drawing unit 104 presents the diagnosis result using a graphical user interface (GUI) 600 as shown in FIG. 6A. FIG. 6A is a diagram showing the GUI that presents a diagnosis result when an image of a breast is received.

The GUI 600 includes a diagnosis result sorting field 601, a display field 602, an image button 603, and a diagnosis result presentation field 604. The diagnosis result sorting field 601 is a field for displaying a class output as the diagnosis result. The corresponding class is highlighted among icons of classes in the diagnosis result sorting field 601. The display field 602 is a field for displaying a value of lesion likelihood calculated by the classification unit 102. The image button 603 is an operation button for displaying an image. The diagnosis result presentation field 604 is a field for displaying the diagnosis result output by the follow-up determination unit 103.

As shown in FIG. 5B, since a malignant tissue/cell (abnormal tissue/cell) are hardly included in the image of the breast, a diagnosis result is sorted into "follow-up" by the follow-up determination unit 103, and a value of lesion likelihood is presented as a sorting basis. The value of the lesion likelihood is a small value (0.08).

When the image button 603 is operated, the drawing unit 104 presents a GUI 610 as shown in FIG. 6B. The GUI 610 displays an input image that is color-coded based on a classification result in order to indicate a region where a classification result is "abnormal" and a region where a classification result is "normal". In FIG. 6B, a hatched region indicates the region where the classification result is "abnormal", and a white region indicates the region where the classification result is "normal". A diagnosis result is superimposed and displayed on the input image. In FIG. 6B, the color-coded input image is presented as a basis for sorting.

Next, the recording unit 105 will be described.

The recording unit 105 stores, in the sub-storage device 203, the input image, the classification intensity of each classification result, the diagnosis result, coordinate information for drawing the input image that is color-coded by the drawing unit 104 according to each classification result, and the like.

The functional units in the image diagnosis support device 1 have been described above. Next, processing executed by the image diagnosis support device 1 will be described.

FIG. 7 is a flowchart showing processing executed by the image diagnosis support device 1 according to the first embodiment. Each processing unit of the image diagnosis support device 1 will be described below as an operation subject. However, the CPU 201 may be as an operation subject, and the CPU 201 may execute each processing unit as a program.

When receiving an input image, the image diagnosis support device 1 starts processing described below.

The input unit 100 inputs the input image to the feature extraction unit 101 (step S701).

The feature extraction unit 101 acquires definition information on a classifier stored in the sub-storage device 203, and calculates the features FAi of a partial image of the input image using the definition information of the classifier (step S702).

Specifically, the feature extraction unit 101 acquires parameters such as the filter coefficient wj and the offset value bi from the sub-storage device 203, and calculates the features FAi using Equation (1).

The classification unit 102 acquires the definition information on the classifier stored in the sub-storage device 203, and calculates the classification intensity y of a classification result of the partial image using the matrix f including the definition information of the classifier and the features FAi (step S703).

Specifically, the classification unit 102 acquires parameters such as the weight matrix w and the offset value b from the sub-storage device 203, and calculates the classification intensity y of the classification result of the partial image using Equation (2).

The classification unit 102 determines whether a tissue/cell included in the partial image is normal or abnormal based on a comparison result between the classification intensity y and a threshold Th1 (step S704).

Specifically, the classification unit 102 determines whether the classification intensity y is equal to or larger than the threshold Th1.

When the classification intensity y is equal to or larger than the threshold Th1, the classification unit 102 sets a value (for example, 1) indicating an abnormal tissue/cell as a classification result res (step S705), and then proceeds to step S707. When the classification intensity y is smaller than the threshold Th1, the classification unit 102 sets a value (for example, 0) indicating a normal tissue/cell as the classification result res (step S706), and then proceeds to step S707.

The classification unit 102 determines whether classification of all the partial images of the input image is completed (step S707).

When the classification of all the partial images of the input image is not completed, the classification unit 102 calls the feature extraction unit 101, and the processing proceeds to step S702. When the classification of all the partial images of the input image is completed, the classification unit 102 calls the follow-up determination unit 103, and the processing proceeds to step S708.

The follow-up determination unit 103 calculates a classification area of each classification result based on the classification result of each of the plurality of partial images, and sorts the input image using the classification intensity and the classification area of each classification result (step S708).

Specifically, the follow-up determination unit 103 sorts the input image into any class of benign, malignant, and follow-up by executing the determination processing described above. The follow-up determination unit 103 calculates a value of lesion likelihood based on the classification intensity of each classification result.

The drawing unit 104 presents a diagnosis result (step 3709).

Specifically, the drawing unit 104 displays, together with the diagnosis result as shown in FIGS. 5A and 5B, the input image that is color-coded based on each classification result as a sorting basis. For example, the drawing unit 104 displays a region classified as "abnormal" with diagonal lines, and a region classified as "normal" in white. As shown in FIG. 6A, the drawing unit 104 displays the diagnosis result and the value of the lesion likelihood as the sorting basis.

The recording unit 105 stores, in the sub-storage device 203, the input image, the classification intensity of each classification result, the diagnosis result, the coordinate information for drawing the input image that is color-coded according to each classification result, and the like (step S710).

As described above, according to the first embodiment, the image diagnosis support device 1 can sort the input image into any one of benign, malignant, and follow-up based on the classification intensity and the classification area of each classification result. This can prevent erroneous detection and excessive detection of a lesion caused by erroneous sorting of benign and malignant.

Second Embodiment

A system using the image diagnosis support device 1 described in the first embodiment will be described in a second embodiment.

FIG. 8 is a diagram showing an example of a configuration of a remote diagnosis support system 800 according to the second embodiment.

The remote diagnosis support system 800 includes a server 801 including an image acquisition device and a server 802 having a function of the image diagnosis support device 1. The two servers 801, 802 are installed at physically separate locations, and are connected to each other via a network 803. The network 803 is a local area network (LAN), a wide area network (WAN), or the like, and a connection method may be wired or wireless.

The server 801 is a computer on which the image acquisition device such as a virtual slide device and a camera is mounted. The server 801 includes an imaging unit 811 that captures an image, and a display unit 812 that displays a diagnosis result transmitted from the server 802.

The server 801 includes an arithmetic device, a storage device, and a communication device that transmits the image to the server 802 and receives data from the server 802, which are not shown.

The server 802 is a computer that executes image processing similar to that of the image diagnosis support device 1 according to the first embodiment. The server 802 includes an image diagnosis support unit 821 that executes image processing according to the first embodiment on the image transmitted by the server 801, a storage unit 822 that stores a diagnosis result output from the image diagnosis support unit 821, and a display unit 823 that displays the diagnosis result output from the image diagnosis support unit 821.

The server 802 includes an arithmetic device, a storage device, and a communication device that transmits the diagnosis result to the server 801 and receives the image from the server 801, which are not shown. The server 802 may include the image diagnosis support unit 821 as hardware equivalent to the image diagnosis support device 1, or may include the image diagnosis support unit 821 as a program.

The image diagnosis support unit 821 classifies presence or absence of an abnormal tissue/cell such as a cancer in the image captured by the imaging unit 811. The image diagnosis support unit 821 sorts lesion likelihood according to a degree of progress (classification intensity) of the abnormal tissue/cell based on a classification result using features of the input image. The image diagnosis support unit 821 sorts the input image into any one of benign, malignant, and follow-up using the classification intensity and a classification area of each classification result, and outputs the sorted result as the diagnosis result.

The display units 812, 823 display the classification result of the input image, the diagnosis result, and the like on screens connected to the servers 801, 802, respectively.

The image acquisition device may be a regenerative medical device including an imaging unit, an iPS cell culture device, and an MRI and ultrasonic imaging device.

According to the second embodiment, a computer (or system) installed at a certain location can sort an image transmitted from 30J a facility or the like at a different location into any one of benign, malignant, and follow-up, and transmit a diagnosis result to the facility or the like at the different location. Accordingly, a computer in the facility or the like that has transmitted the image can display the diagnosis result. In this way, the remote diagnosis support system can be provided according to the second embodiment.

Third Embodiment

A system using the image diagnosis support device 1 described in the first embodiment will be described in a third embodiment.

FIG. 9 is a diagram showing an example of a configuration of a network consignment service providing system 900 according to the third embodiment.

The network consignment service providing system 900 includes a server 901 including an image acquisition device and a server 902 having a function of the image diagnosis support device 1. The two servers 901, 902 are installed at physically separate locations, and are connected to each other via a network 903. The network 903 is a local area network (LAN), a wide area network (WAN), or the like, and a connection method may be wired or wireless.

The server 901 is a computer on which the image acquisition device such as a virtual slide device and a camera is mounted. The server 901 includes an imaging unit 911 that captures an image, a storage unit 912 that stores classifier information transmitted from the server 902, and an image diagnosis support unit 913 that executes image processing according to the first embodiment on the image newly captured by the imaging unit 911 using the classifier information.

The server 901 includes an arithmetic device, a storage device, and a communication device that transmits the image to the server 902 and receives the classifier information from the server 902, which are not shown. The server 901 may include the image diagnosis support unit 913 as hardware equivalent to the image diagnosis support device 1, or may include the image diagnosis support unit 913 as a program.

The server 902 is a computer that executes image processing similar to that of the image diagnosis support device 1 according to the first embodiment. The server 902 includes an image diagnosis support unit 921 that executes the image processing according to the first embodiment, and a storage unit 922 that stores the classifier information output from the image diagnosis support unit 921.

The server 902 includes an arithmetic device, a storage device, and a communication device that transmits the classifier information to the server 901 and receives the image from the server 901, which are not shown. The server 902 may include the image diagnosis support unit 921 as hardware equivalent to the image diagnosis support device 1, or may include the image diagnosis support unit 921 as a program.

The server 902 executes the image processing according to the first embodiment on the image captured by the imaging unit 911, and executes machine learning for generating a classifier (model) for correctly classifying a normal tissue/cell and an abnormal tissue/cell. Here, the classifier includes the feature extraction unit 101 and the classification unit 102. The server 902 transmits the classifier information, which is definition information on the classifier, to the server 901 installed in a facility or the like at a different location.

When performing actual diagnosis, the server 901 reads the classifier information from the storage unit 912, and executes classification processing and sorting processing on the image captured by the imaging unit 911 using the classifier defined by the classifier information.

The image acquisition device may be a regenerative medical device including an imaging unit, an iPS cell culture device, and an MRI and ultrasonic imaging device.

The server 902 may execute learning processing a plurality of times using images having different characteristics in advance using the image diagnosis support unit 921, and store a plurality of pieces of classifier information in the storage unit 922. When receiving the image from the server 901, the server 902 executes classification processing and sorting processing using the image diagnosis support unit 921 in which classifiers are set, and transmits the classifier information on the classifier with the highest accuracy to the server 901.

According to the third embodiment, a computer (or a system) installed at a certain location can generate a classifier using an image transmitted from a facility or the like at a different location and transmit information on the classifier to the facility or the like at the different location. Accordingly, a computer in the facility or the like that has transmitted the image can output a diagnosis result of any one of benign, malignant, and follow-up for a new image. In this way, the network consignment service providing system can be applied according to the third embodiment.

The embodiments described above can be modified as follows.

The feature extraction unit 101 calculates the features using a filter (CNN or the like) generated by machine learning, or may use other features such as HOG to achieve the same effects.

The feature extraction unit 101 calculates the features using one classifier for an input image, or may calculate the features using two or more classifiers to achieve the same effects.

The classification unit 102 executes logistic regression processing to classify a tissue/cell, or may use linear regression, Poisson regression, or the like to achieve the same effects.

The invention is not limited to the embodiments described above, and includes various modifications. For example, the embodiments described above have been described in detail for easy understanding of the invention, and the invention is not necessarily limited to those including all the configurations described above. Some configuration of the embodiments can be added to, deleted from, or replaced with another configuration.

In addition, some or all of the above configurations, functions, processing units, processing methods, and the like may be implemented by hardware through, for example, design using an integrated circuit. Further, the invention can also be implemented by a program code of software that implements the functions of the embodiments. In this case, a storage medium recording the program code is provided on a computer, and a processor in the computer reads the program code stored in the storage medium. In this case, the program code itself read from the storage medium implements the functions of the above embodiments, and the program code itself and the storage medium storing the program code constitute the invention. Examples of the storage medium for supplying such a program code include a flexible disk, a CD-ROM, a DVD-ROM, a hard disk, a solid state drive (SSD), an optical disk, a magneto-optical disk, a CD-R, a magnetic tape, a nonvolatile memory card, and a ROM.

The program code that implements the functions described in the present embodiment can be implemented in a wide range of programs or script languages such as assembler, C/C++, perl, Shell, PHP, Python, and Java (registered trademark).

Further, the program code of the software that implements the functions of the embodiments may be distributed via a network to be stored in a storage unit such as a hard disk or a memory of a computer or a storage medium such as a CD-RW or a CD-R, and a processor in the computer may read and execute the program code stored in the storage unit or the storage medium.

In the embodiments described above, control lines and information lines that are considered to be necessary for description are shown, and not all control lines and information lines are necessarily shown on a product. All configurations may be interconnected.

The invention claimed is:

1. An image diagnosis method executed by an image diagnosis support device including one or more processors, a storage device, and a connection interface configured to connect to an external device, the image diagnosis method comprising:

acquiring, by the one or more processors via the connection interface, an image including at least one element corresponding to a tissue or a cell, and storing the image in the storage device;

for each partial image of a plurality of partial images that are part of the image and include the at least one element, classifying, by the one or more processors, a property of the at least one element included in the partial image, and storing a classification result in the storage device;

sorting, by the one or more processors, the image into any one of benign indicating that no lesion element is present, malignant indicating that a lesion element is present, and follow-up, based on classification results of the plurality of partial images, and storing a sorting result as a diagnosis result in the storage device; and outputting, by the one or more processors, the diagnosis result via the connection interface, wherein the classifying includes calculating, by the one or more processors, for each partial image of the plurality of partial images and for each of a plurality of properties including at least a normal property and an abnormal property, a classification intensity indicating a degree to which the at least one element included in the partial image corresponds to the property, and storing, in the storage device, the classification result including the classification intensity for each of the plurality of properties, and wherein the sorting includes:

calculating, by the one or more processors, for the abnormal property, a classification area in the image based on the classification result of each of the plurality of partial images, the classification area being based on a number of pixels of a tissue region in the image having the abnormal property;

comparing, by the one or more processors, a classification intensity for the abnormal property with a first classification-intensity threshold and a second classification-intensity threshold smaller than the first classification-intensity threshold, and comparing the classification area for the abnormal property with a first area-percentage threshold and a second area-percentage threshold larger than the first area-percentage threshold; and sorting the image into any one of the benign, the malignant, and the follow-up based on results of the comparisons, including:

determining that the image is malignant when there exists a region of the image in which the classification intensity for the abnormal property is greater than or equal to the first classification-intensity threshold;

when no such region exists, determining that the image is benign when a classification area for regions of the image in which the classification intensity for the abnormal property is less than the first classification-intensity threshold and greater than or equal to the second classification-intensity threshold is less than the first area-percentage threshold;

determining that the image is follow-up when the classification area for the regions is greater than or equal to the first area-percentage threshold and less than the second area-percentage threshold; and determining that the image is malignant when the classification area for the regions is greater than or equal to the second area-percentage threshold.

2. The image diagnosis method according to claim 1, wherein outputting the diagnosis result includes outputting, by the one or more processors via the connection interface, basis information on the sorting of the image together with the diagnosis result.

3. The image diagnosis method according to claim 2, wherein the basis information includes at least one of an image indicating the classification area for the abnormal property and a value indicating a degree of lesion likelihood calculated based on the classification intensity for each of the plurality of properties.

4. The image diagnosis method according to claim 2, wherein outputting the diagnosis result and the basis information includes displaying, on a graphical user interface, (a) an image color-coded according to classification results for the plurality of properties, (b) an indication of which of benign, malignant, and follow-up has been selected as the diagnosis result, and (c) the value indicating the degree of lesion likelihood.

5. The image diagnosis method according to claim 1, wherein classifying the property of the at least one element included in each partial image of the plurality of partial images includes extracting, by the one or more processors, features of the partial image using a convolutional neural network and calculating, for each of the plurality of properties, the classification intensity by applying logistic regression to the extracted features.

6. The image diagnosis method according to claim 1, wherein calculating the classification area for the abnormal property includes detecting, by the one or more processors, the tissue region in the image and calculating the classification area for the abnormal property as a percentage of pixels in the tissue region for which the abnormal property is classified.

7. An image diagnosis support device comprising:

one or more processors;

a storage device; and a connection interface configured to connect to an external device;

wherein the one or more processors are collectively configured to:

acquire, via the connection interface, an image including at least one element corresponding to a tissue or a cell, and store the image in the storage device;

for each partial image of a plurality of partial images that are part of the image and include the at least one element, classify a property of the at least one element included in the partial image, and store a classification result in the storage device;

sort the image into any one of benign indicating that no lesion element is present, malignant indicating that a lesion element is present, and follow-up, based on classification results of the plurality of partial images, and store a sorting result as a diagnosis result in the storage device; and output the diagnosis result via the connection interface;

wherein the one or more processors are further configured to calculate, for each partial image of the plurality of partial images and for each of a plurality of properties including at least a normal property and an abnormal property, a classification intensity indicating a degree to which the at least one element included in the partial image corresponds to the property, and to store, in the storage device, the classification result including the classification intensity for each of the plurality of properties, and wherein the one or more processors are further configured to:

calculate, for the abnormal property, a classification area in the image based on the classification result of each of the plurality of partial images, the classification area being based on a number of pixels of a tissue region in the image having the abnormal property;

compare a classification intensity for the abnormal property with a first classification-intensity threshold and a second classification-intensity threshold smaller than the first classification-intensity threshold, and compare the classification area for the abnormal property with a first area-percentage threshold and a second area-percentage threshold larger than the first area-percentage threshold; and sort the image into any one of the benign, the malignant, and the follow-up based on results of the comparisons, including:

determining that the image is malignant when there exists a region of the image in which the classification intensity for the abnormal property is greater than or equal to the first classification-intensity threshold;

when no such region exists, determining that the image is benign when a classification area for regions of the image in which the classification intensity for the abnormal property is less than the first classification-intensity threshold and greater than or equal to the second classification-intensity threshold is less than the first area-percentage threshold;

determining that the image is follow-up when the classification area for the regions is greater than or equal to the first area-percentage threshold and less than the second area-percentage threshold; and determining that the image is malignant when the classification area for the regions is greater than or equal to the second area-percentage threshold.

8. The image diagnosis support device according to claim 7, wherein the one or more processors are configured to output, via the connection interface, basis information on the sorting of the image together with the diagnosis result.

9. The image diagnosis support device according to claim 8, wherein the basis information includes at least one of an image indicating the classification area for the abnormal property and a value indicating a degree of lesion likelihood calculated based on the classification intensity for each of the plurality of properties.

10. The image diagnosis support device according to claim 7, wherein the one or more processors are configured to calculate, for each partial image of the plurality of partial images and for each of the plurality of properties, the classification intensity by performing logistic regression on features obtained from the partial image by a convolutional neural network.

11. A computer system comprising:

the image diagnosis support device according to claim 7; and a computer configured to capture an image to be processed and transmit the image to be processed to the image diagnosis support device via a network.

12. The computer system according to claim 11, wherein, when receiving the image to be processed from the computer, the one or more processors of the image diagnosis support device are configured to transmit, to the computer via the network, a diagnosis result for the image to be processed.

13. The computer system according to claim 11, wherein:

the computer includes an imaging device, one or more processors, and a memory storing instructions that cause the computer to implement operations corresponding to acquiring the image to be processed, classifying properties of elements included in partial images of the image to be processed, sorting the image to be processed into any one of benign, malignant, and follow-up based on classification results of a plurality of the partial images of the image to be processed, and outputting a diagnosis result for the image to be processed, and wherein:

when receiving the image to be processed from the computer, the one or more processors of the image diagnosis support device are configured to generate information on a classifier for implementing the classifying so as to obtain a correct diagnosis result for the image to be processed and to transmit the information on the classifier to the computer; and the one or more processors of the computer are configured to acquire a diagnostic image and to output a diagnosis result of the diagnostic image using the information on the classifier.

14. The computer system according to claim 11, wherein the image diagnosis support device is implemented on a first server and the computer is implemented on a second server installed at a different location, the first and second servers being connected via a wide area network and configured such that the diagnosis result indicating benign, malignant, or follow-up for the image to be processed is transmitted from the first server to the second server for display.

* * * * *